United States Patent
Luckman et al.

[11] Patent Number: 5,968,051
[45] Date of Patent: Oct. 19, 1999

[54] PATELLA CLAMPING DEVICE

[75] Inventors: Thomas Luckman, Falmouth; Ernest Quintanilha, Norton, both of Mass.

[73] Assignee: Johnson & Johnson Professional, Inc., Raynham, Mass.

[21] Appl. No.: 08/508,181

[22] Filed: Jul. 27, 1995

[51] Int. Cl.⁶ .................................................. A61B 17/56
[52] U.S. Cl. ................................................ 606/88; 606/86
[58] Field of Search .................. 606/86, 87, 88, 606/205, 206, 207, 208, 218; 81/314, 318–325, 328, 336–338, 352–357

[56] References Cited

U.S. PATENT DOCUMENTS

| | | | |
|---|---|---|---|
| 1,426,553 | 8/1922 | Cruickshank | 81/328 |
| 1,985,108 | 12/1934 | Rush | 128/346 |
| 2,181,746 | 11/1939 | Siebrandt | 128/83 |
| 2,291,413 | 7/1942 | Siebrandt | 128/83 |
| 2,427,128 | 9/1947 | Ettinger | 128/346 |
| 2,460,470 | 2/1949 | Rogers | 128/346 |
| 2,583,896 | 1/1952 | Siebrandt | 128/346 |
| 2,631,585 | 3/1953 | Siebrandt | 128/92 |
| 4,364,381 | 12/1982 | Sher et al. | 128/92 E |
| 4,633,862 | 1/1987 | Petersen | 128/92 VY |
| 4,706,660 | 11/1987 | Petersen | 128/92 VW |
| 5,002,547 | 3/1991 | Poggie et al. | 606/88 |
| 5,108,401 | 4/1992 | Insall et al. | 606/79 |
| 5,129,908 | 7/1992 | Petersen | 606/88 |
| 5,284,482 | 2/1994 | Mikhail | 606/86 |

*Primary Examiner*—Michael Buiz
*Assistant Examiner*—David O. Reip
*Attorney, Agent, or Firm*—Nutter, McClennen & Fish, LLP

[57] ABSTRACT

A patella clamping device includes a handle portion and a clamp portion. The clamp comprises at least two jaw members that are pivotally joined to one another in a scissors-like orientation. A ratchet mechanism is associated with the device to ensure locking of the clamp in the closed position. A guide mechanism is also provided with the device to ensure a vertical, coaxial closing action of the clamp element.

22 Claims, 6 Drawing Sheets

PATELLA CLAMPING DEVICE

BACKGROUND OF THE INVENTION

The invention relates to a clamping device to facilitate affixation of a prosthetic patella component to the natural patella during knee arthroplasty procedures.

Knee arthroplasty procedures require the resection of the natural articulation surface of the patella and replacement thereof with a prosthetic patella component. Subsequently, through known procedures, the resected surface of the patella is reamed to form a cavity that can accept the patella prosthesis. The cavity is filled with bone cement and the patella prosthesis is inserted within the cavity. Thereafter, the natural patella and the prosthesis must be held together firmly until the cement cures. Typically a special clamping device is used to hold and apply pressure to these components.

A number of clamping devices are known to exist. For example, U.S. Pat. Nos. 5,284,482; 5,129,908; and 4,706,660 all disclose various patella clamping devices. These patents describe clamp devices that require two hand operation: one hand closes the clamp while the other uses a thumb screw or a similar device to lock the clamp in the closed position. The design of the disclosed clamps is such that the closing motion of the clamp is non-linear.

Patella clamping devices generally include two jaw elements that close together to engage and hold firmly the prosthetic patella component and the natural patella. It is desirable for the jaws to close together in a consistent manner with a linear application of force so that the components are not drawn out of alignment while the load is applied. Once the jaws are closed to apply the load to the two components, the jaws must be held together firmly with a constant application of pressure. To accomplish this, it is often necessary to lock the jaws in place.

Many patella clamps have locking devices to maintain the jaws of the clamp in the closed, load applying position. Known clamp designs, such as those described in the references noted above, usually require the surgeon to maintain pressure on the clamping jaws with one hand while using the other hand to actuate the locking mechanism. The necessity for the surgeon to use two hands during the locking procedure can be inconvenient. It would thus be advantageous to provide a clamping device that enables the linear application of load and which enables locking of the device using only one hand.

Many patella clamps also do not permit the clamping members to close with a vertical or linear application of load. A non-linear closing motion of a clamp could result in the application of forces which cause misalignment of the patella components while the clamping load is applied.

Accordingly, an object of the invention is to provide a patella clamping device that enables the linear application of clamping load and the ability to lock the clamping jaws in place using only one hand. It is also an object of the invention to provide a patella clamp that can be used with greater ease and accuracy. Further objects will be apparent to those having ordinary skill in the art on reading the disclosure that follows.

SUMMARY OF THE INVENTION

The invention provides a clamping device that is adapted to join together and to maintain load on the natural patella and a patella prosthesis during the knee arthroplasty procedures. The patella clamping device of the invention includes first and second opposed jaw members that are joined to each other at a pivot point in a scissors-like orientation. The jaw members each include a distal clamping portion and a proximal handle portion. Due to the scissors-like orientation of the jaw members, a force applied to close together the jaw members that form the handle portion results in closing of the jaw members that form the clamp portion. Preferably, the clamp device also includes an element that biases the jaw members of the clamp portion to the open position.

In a preferred embodiment the clamp device includes a linear bearing member that ensures a vertical application of clamping load by the clamping portion of the device, while at the same time allows the clamp elements to close in a coaxial motion. The linear bearing member can include an elongate, vertically extending member that is rigidly affixed to one of the first or second jaw members, preferably at a location intermediate of the pivot point and the distal end of the clamping portion. The elongate member extends vertically toward the other of the first or second jaw members and includes a vertically-orientated slot within which the other of the first or second jaw members is mounted and adapted for vertical travel. In a preferred embodiment the biasing element is disposed within the linear bearing member.

The patella clamp device of the invention is also advantageous as it includes a selectively engageable ratchet mechanism which, when engaged, permits closure of the jaw members, but prevents further opening of the jaw members. Preferably, the ratchet mechanism includes a plurality of inclined teeth that are disposed on a surface of one of the first or second jaw members. In addition, a pawl member is mounted on the other of the first or second jaw members such that it is selectively engageable with the inclined teeth. The ratchet also includes a locking device which is readily accessible to a surgeon using the same hand that manipulates the clamp, to selectively engage or disengage the pawl member.

Proper vertical, coaxial closing action of the clamping elements can be achieved by forming a joint in the jaw member that travels within the slot, thus forming segmented portions of this jaw member. The segmented portions of the jaw member are thus able to articulate within the bearing member.

DETAILED DESCRIPTION OF THE INVENTION

FIGS. 1 through 7 illustrate the patella clamping device 10 of the invention in which first and second jaw members 12, 14 are joined at a pivot point 16 in a scissors-like orientation. The jaw members 12, 14, when joined at pivot point 16, have a clamping portion 18 distal of the pivot point and a handle portion 20 proximal of the pivot point.

The handle portion 20 includes opposed handle members 22, 24 which are biased apart from one another. The clamp portion 18 includes a lower clamping arm 26 and a segmented, upper clamping arm 28. Segmented upper clamping arm 28 includes a proximal segment 30 and a distal segment 32. Horizontally oriented patella engaging disks 34, 36 form a distal end of lower clamp arm 26 and distal segment 32 of upper clamp arm 28.

The lower disk 34 is annularly shaped, having a central aperture 37 formed therein. This disk is adapted to seat the anterior surface of the natural patella (not shown) and includes bone penetrating spikes 38 extending from an annular surface 40 to securely seat the patella.

Upper disk 36 is also annularly shaped and includes a central aperture 42 formed therein. This disk is adapted to seat the articulation surface of a patella prosthesis 41, and preferably includes a cushioning material, such as O-ring 44, formed in a recess 46 of the disk. The clamp device 10 also includes a ratchet mechanism 48 that has inclined teeth 50 mounted on a surface of the first jaw member 12 and a selectively engageable pawl 52 mounted on second jaw member 14. Preferably, the ratchet is disposed in proximity to the pivot point 16.

A linear bearing member 54 is also present on the clamp 10 to ensure that the clamping disks 34, 36 close together coaxially in a linear vertical motion. Linear bearing member 54 preferably is connected between the lower clamp arm 26 and the upper, segmented clamp arm 28.

Referring to FIGS. 3A, 3B, 3C, 3D, 4A and 4B, first jaw member 12 has a horizontally oriented handle member 22, an intermediate vertical portion 56, and a horizontally oriented upper, segmented clamp arm 28. The upper clamp arm 28 includes separate segments formed by proximal segment 30, shown in FIG. 3B, which is integral with vertical portion 56 and handle member 22, and a separate distal segment 34 which is integral with clamping disk 36. Preferably, the distal end of the first jaw member 22 includes a flange portion 60 which abuts a portion of the second jaw member 14 to control the distance between the handle members 22, 24 when the clamp is in the open position.

The first jaw member also includes a ratchet flange 62 which preferably extends from a portion of the jaw member between the vertical portion 56 and the proximal segment 30. An upper surface of the ratchet flange 62 includes inclined teeth 50. Each tooth 50 has an apex 64, a pawl engaging face 66 on a rear-facing side of the apex, and a ramped surface 68 on a forward-facing side of the apex. Each tooth 50 preferably has a height of about 0.020–0.040 inch and most preferably about 0.030 inch. The ramped surface 68 of each tooth preferably is oriented at a nominal angle of about 45 degrees.

The second jaw member 14 includes a horizontally extending handle member 24, intermediate vertical portion 70, and a horizontally extending clamp arm 26. The vertical portion 70 preferably includes a slot 72 that is adapted to receive the vertical portion 56 of the first jaw member 12. Preferably, pivot 16 extends through the mated vertical portions 56, 70 of the first and second jaw members 12, 14 to allow a pivotal, scissors-like motion of the two members. In one preferred embodiment, the lower clamp arm 26 includes a mounting aperture 74 within which one end of the linear bearing member 54 can mount.

Figure 6:
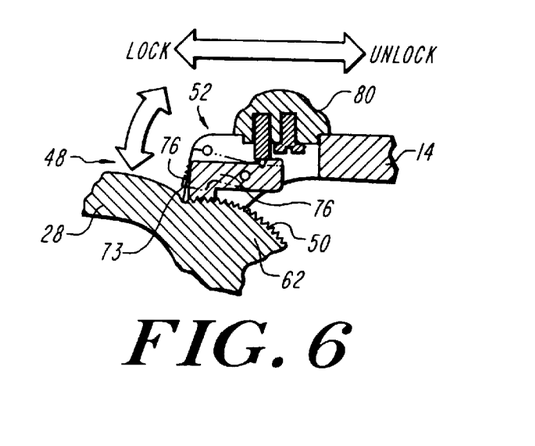
FIG. 6 is a detailed side, sectional view of the ratchet and pawl mechanism shown in FIG. 1.

A pawl mechanism 52 preferably is mounted on the second jaw member 14 at a distal portion of the handle member 24, in proximity to vertical portion 70. The pawl mechanism includes a pawl member 76 having one or more teeth 73 that engage inclined teeth 50 of ratchet 48. The pawl member 76 preferably is pivotally mounted upon the second handle member 24 of jaw member 14. A locking member 80 also is mounted on the top surface of the second handle portion 24 and is adapted for linear movement, forward and backward, to engage (lock) and disengage (unlock) the pawl member 76. FIG. 6 illustrates the pawl member 76 in the locked position in which it engages the teeth 50 of ratchet 48 and in the unlocked position (in phantom). When pawl mechanism 52 is locked the clamp device can be closed, but it cannot be opened until the locking mechanism is released.

Figure 1:
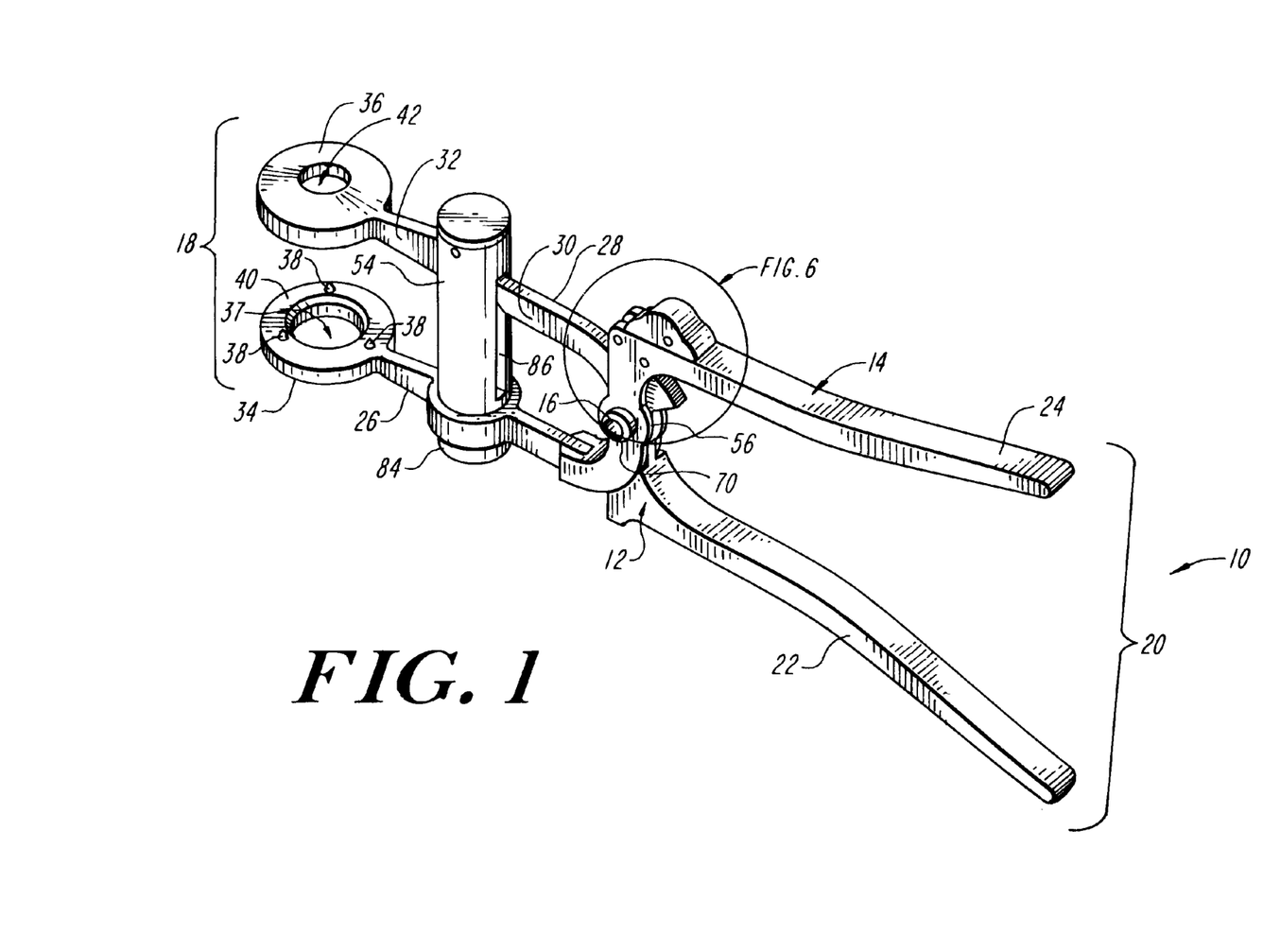
FIG. 1 is a perspective view of the patella clamp device of the present invention.
Figure 1A:
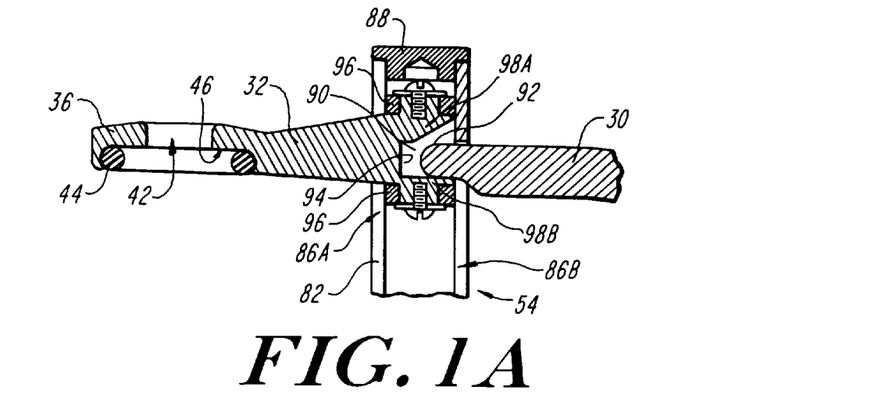
FIG. 1A is a side sectional view of the clamping portion of one of the jaw members of the clamp device.
Figure 2:
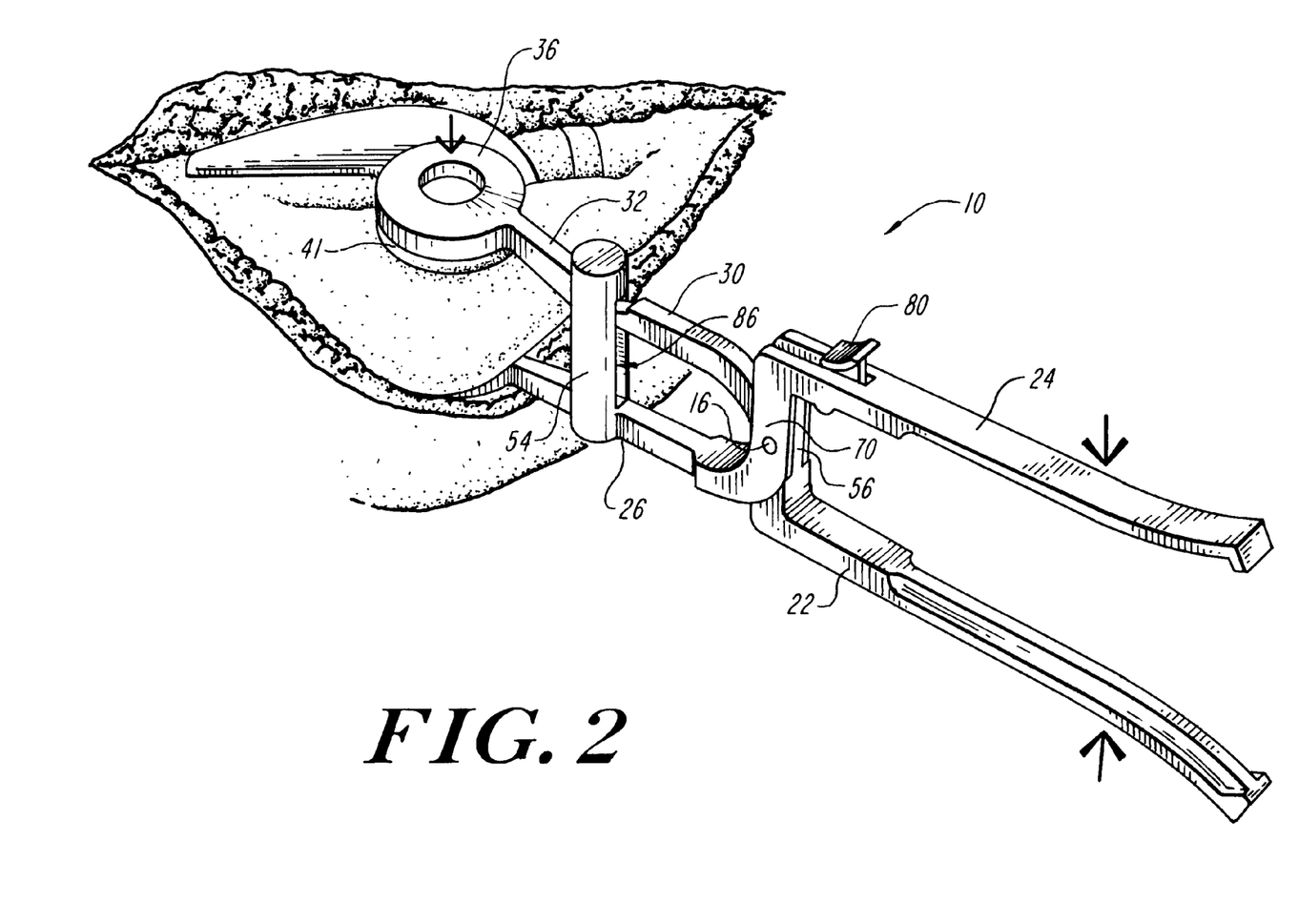
FIG. 2 illustrates the patella clamp device of FIG. 1 used to engage and maintain a natural patella and a patella prosthesis in contact with one another.
Figure 3A:
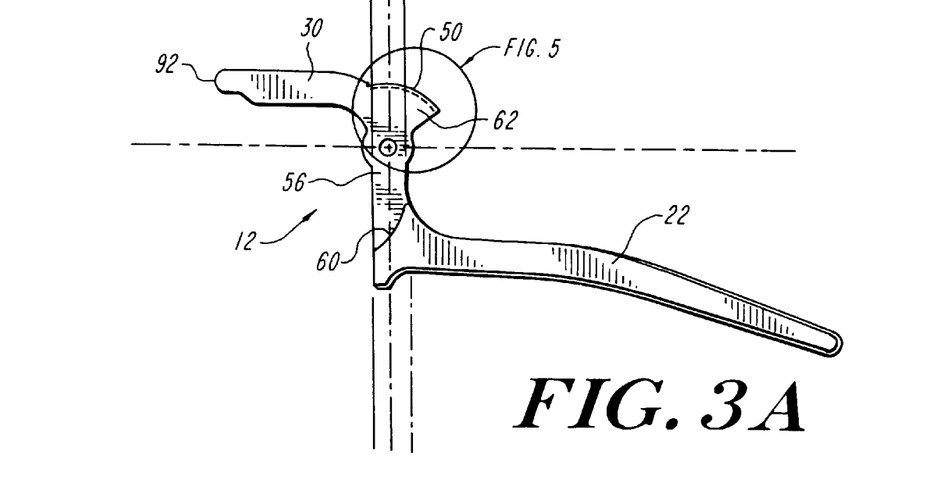
FIG. 3A is a side view of a proximal portion of a first jaw member including a ratchet.
Figure 3B:
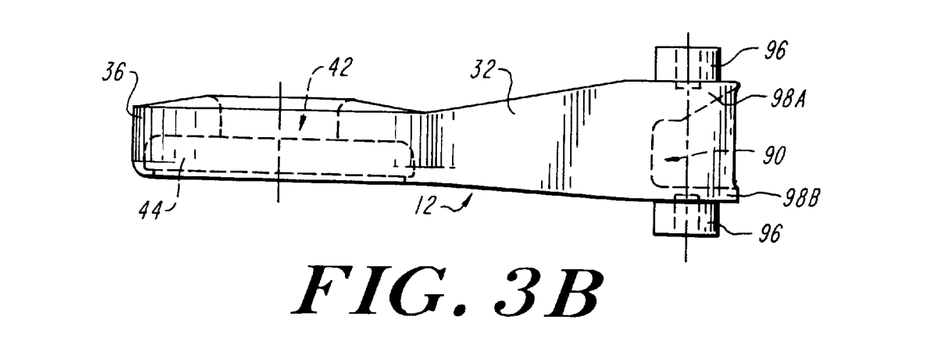
FIG. 3B is a side view of a distal segment of the first jaw member that mates with the proximal portion of the first jaw member shown in FIG. 3A.
Figure 3C:
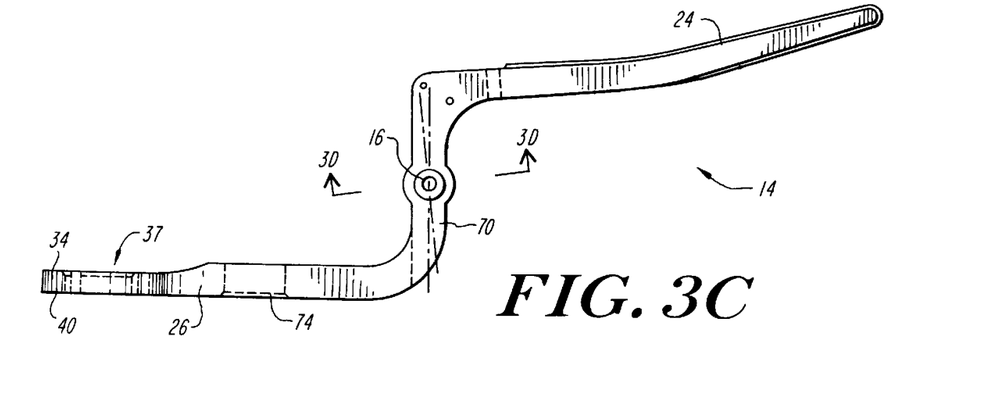
FIG. 3C is a side view of the second jaw member.
Figure 3D:
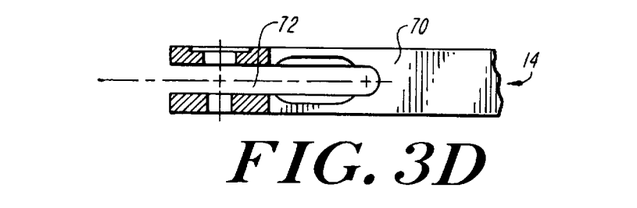
FIG. 3D is a sectional view of the jaw member shown in FIG. 3C at lines 3D—3D.
Figure 4A:
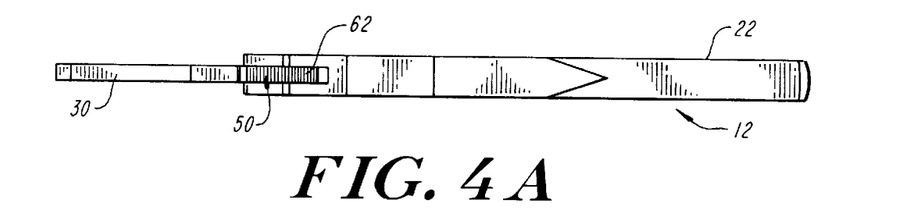
FIG. 4A is a top view of the proximal portion of the first jaw member shown in FIG. 3A.
Figure 4B:
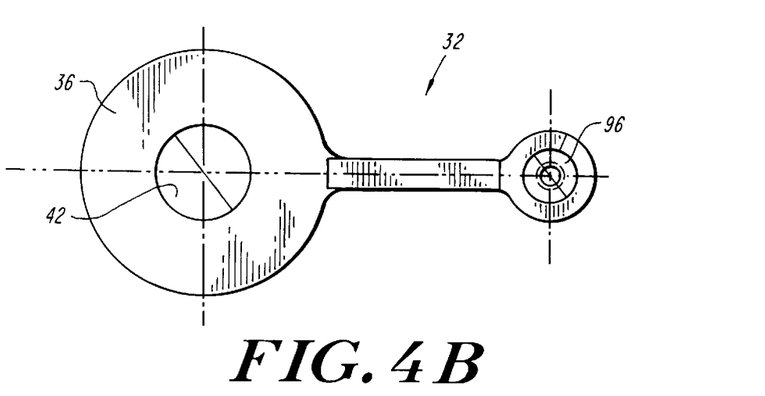
FIG. 4B is a top view of the distal portion of the second jaw member shown in FIG. 3B.
Figure 4C:
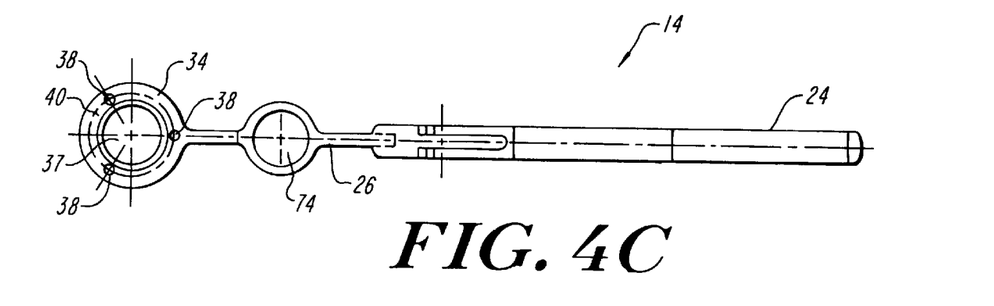
FIG. 4C is a top view of the second jaw member shown in FIG. 3C.
Figure 5:
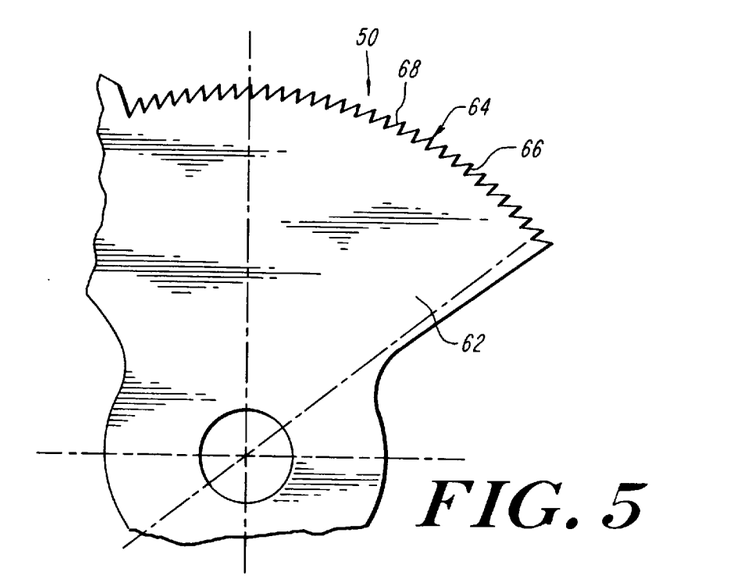
FIG. 5 is a detailed view of the ratchet portion of the jaw member shown in FIG. 3A.
Figure 7:
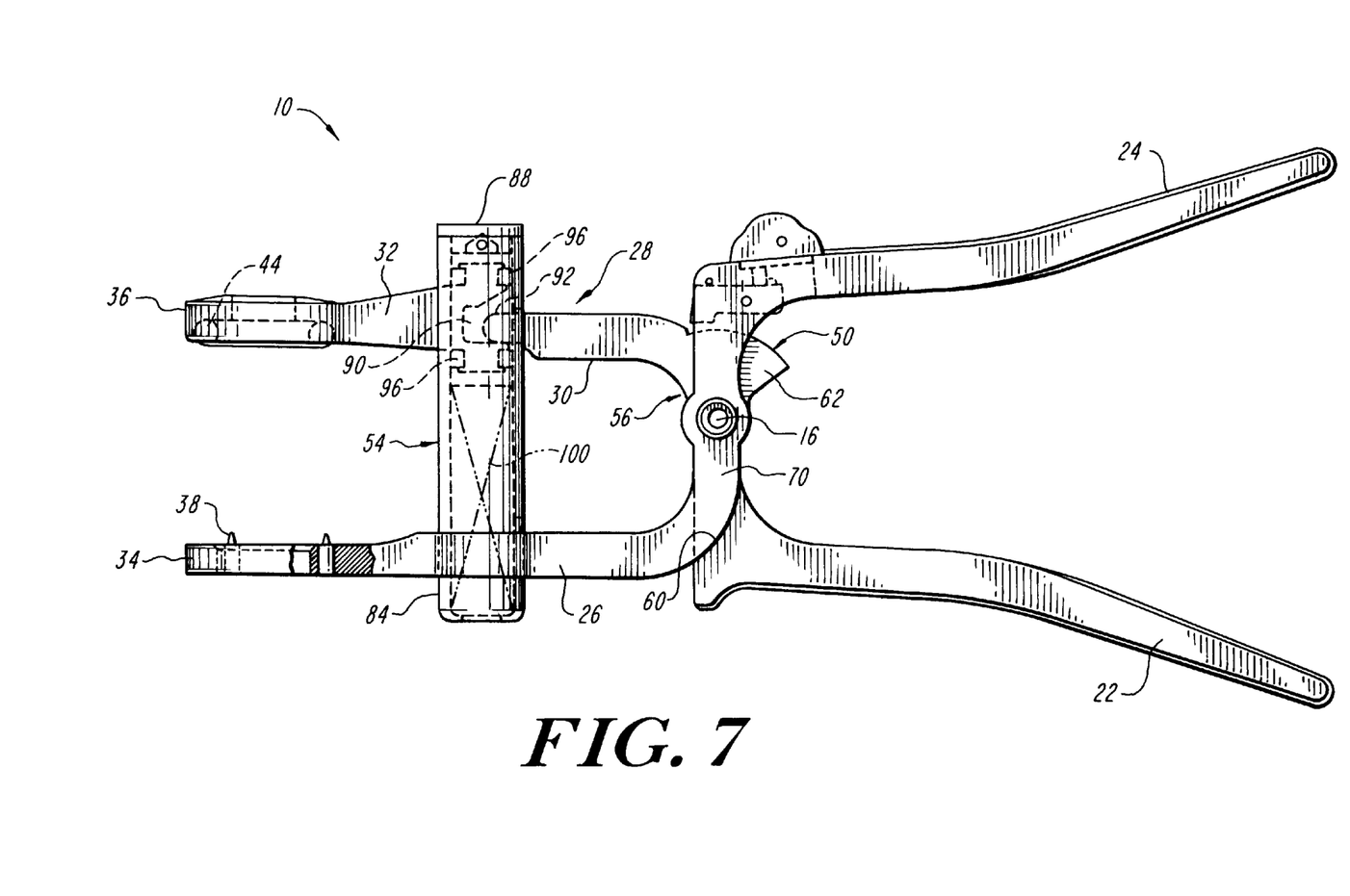
FIG. 7 is a side, partially cut-away view of the patella clamp device shown in FIG. 1.

Linear bearing member 54 forms a guide that facilitates the linear, vertical closing action of disks 34, 36 with a coaxial closing motion. As illustrated in FIGS. 1A and 7, linear bearing member 54 includes an elongate member 82, preferably cylindrical in shape, which extends between the lower clamp arm 26 and the upper, segmented clamp arm 28. In a preferred embodiment the lower end 84 of elongate member 82 is rigidly secured to lower clamp arm 26. Preferably, the lower end 84 mounts within mounting aperture 74 of lower clamp arm 26 and is welded within the aperture.

The elongate member 82 preferably is in the form of a cylindrical member having coaxial, vertically extending slots 86 formed therein. Preferably, forward and rear facing slots 86A, 86B are formed within the member 82. The forward facing slot 86A preferably extends from the top to the bottom of the member 82 while the rear facing slot extends to a position just below the top of member 82. Preferably, a removable cap 88 is mounted to a top portion of the elongate member 82 to close the top thereof.

As noted, upper clamp arm 28 is segmented and has proximal and distal segments 30, 32. The proximal and distal segments 30, 32 form a joint 90 that is housed within elongate member 82. The joint 90 enables articulation of the proximal and distal segments 30, 32 as the clamp is closed. The articulation of these segments enables the disks 34,36 to close together coaxially in a linear vertical motion. This closing action is beneficial as it ensures that the patella components will not be subjected to skewing or misaligning forces as they are clamped together.

As shown in FIGS. 1A and 7, joint 90 is formed by the engagement of a male mating member 92 of proximal segment 30 within a vertically oriented female slot 94 formed by the proximal end of distal segment 32. Further, a low friction bearing element 96 is mounted to the upper and lower portions 98A, 98B of female slot 94. A spring mechanism 100, or another suitable biasing element, is preferably dispersed within the elongate member 82 of the linear bearing member 54 to bias the clamp to the open position. Preferably, the spring is disposed below the lower portion 98B.

The low friction bearing element 96 can be made from a variety of known durable polymeric materials that exhibit a low coefficient of friction. Silicone is an example of one material from which bearing element 96 may be made.

The clamp of the present invention can be used in the following manner. Once the patella is everted and resected, the resected surface thereof is reamed to form one or more cavities that will facilitate mounting of the patella prosthesis. These cavities are filled with a bone cement and the patella prosthesis is then joined to the natural patella. The locking mechanism 80 of the ratchet 48 is switched to the locked position and the handle members are closed together, thus closing together disks 34, 36 while applying pressure to the patella and the patella prosthesis. The clamp device is utilized such that lower disk 34 engages the anterior surface of the natural patella while the upper disk 36 engages the articulation surface of the patella prosthesis. Once the appropriate level of pressure is applied the clamp remains in the closed position, through the action of the ratchet, until the bone cement cures. Thereafter, the locking mechanism can be switched to the unlocked position and the clamp removed from the patella and the patella prosthesis.

The design of the present clamping device is such that it improves the ease of operation of the clamping device as well as its effectiveness. The device may be operated by a surgeon using one hand such that the clamp is closed about the patella and the patella prosthesis and remains in the closed position. Moreover, the linear bearing member ensures that the clamping action of the clamping disks achieves a linear vertical motion and that the disks remain coaxially oriented while they are closed. This ensures that the patella and patella prosthesis are not misaligned during the clamping process.

Those of ordinary skill in the will appreciate the patella clamp of the present invention can be made from a variety of materials that are well suited for use in manufacturing a reusable, sterilizable medical devices. Surgical grade stainless steel is a preferred material from which the clamp can be manufactured. Moreover, one of ordinary skill in the art will appreciate that the clamp can be manufactured in a variety of sizes and dimension. Generally, however, the device is approximately 8 to 10 inches in overall length and about 3 to 5 inches in height. Clamping disks can have a diameter of about 0.5 to 1.5 inch. Also, the length of the clamped portion of the device ranges from about 3 to 5 inches while the length of the handle portion of the device ranges from about 4 to 6 inches.

The foregoing description of the illustrative embodiments of the invention is provided to indicate the range of constructions to which the invention applies. Variations in the physical architecture and dimensions of the patella clamp device will be apparent to those having ordinary skill in the art based upon the disclosure herein, and such variations are considered to be within the scope of the invention in which patent rights are asserted, as set forth in the claims appended hereto.

What is claimed is:

1. A patella clamp device, comprising:
   first and second opposed jaw members joined to each other at a pivot point, each jaw member having a clamping portion distal to the pivot point and a handle portion proximal to the pivot point, with a first one of the first and second jaw members having a proximal segment and a distal segment coupled at a flexible joint;
   a disk-like engaging member appended to the distal end of each of the jaw members; and
   a guide disposed on and connecting the first and second jaw members at a position intermediate of the pivot point and the clamp portion of the jaw members with at least a portion of said guide disposed over the flexible joint.

2. The device of claim 1 wherein said guide comprises:
   a linear bearing member rigidly affixed at one end to a first one of the first and second jaw members, the linear bearing member including an elongate member having at least one elongate, vertically oriented slot therein for receiving and permitting vertical travel of the other of the first or second jaw members; and
   a means for biasing the clamp portion and the handle portion of the first and second jaw members apart from each other.

3. The device of claim 1, further comprising:
   a plurality of inclined teeth disposed on a surface of an intermediate portion of one of the first or second jaw members;
   a pawl member mounted on an intermediate portion of the other of the first or second jaw members, the pawl member being selectively engageable with the inclined teeth such that the pawl member, in the engaged position, permits closing of the jaw members but prevents opening of the jaw members; and
   means for selectively engaging the pawl member.

4. The device of claim 3 wherein the inclined teeth are mounted on a surface of the first jaw member in proximity to the pivot point.

5. The device of claim 4 wherein the inclined teeth have an apex, a substantially vertical surface on one side of the apex adapted to engage the pawl member, and a ramped surface on the other side of the apex.

6. The device of claim 5 wherein the pawl member is disposed within the second jaw member, proximal to the pivot point and in proximity to the surface of the first jaw member bearing the inclined teeth.

7. The device of claim 6 wherein a locking switch is mounted on a surface of the second jaw member to selectively engage and disengage the pawl member.

8. The device of claim 7 wherein the locking switch reciprocates linearly between a locked position in which the pawl engages the inclined teeth and an unlocked position in which the pawl is disengaged from the inclined teeth.

9. The device of claim 1 wherein each disk-like engaging member has an aperture disposed therein.

10. The device of claim 1 wherein a first disk-like engaging member includes a mounting cushion on a surface thereof adapted to engage the articulation surface of a patella prosthesis.

11. The device of claim 10 wherein the mounting cushion is an O-ring.

12. The device of claim 1 wherein a second disk-like engaging member includes means for engaging and securing the anterior surface of a natural patella.

13. The device of claim 12 wherein the means for engaging comprises a plurality of bone engaging spikes.

14. A patella clamp device, comprising:
   first and second opposed jaw members joined to each other at a pivot point, each jaw member having a clamping portion distal to the pivot point and a handle portion proximal to the pivot point, the pivotal joinder of the first and second jaw members being such that force exerted to overcome a biasing force on the jaw members to draw together the jaw members of the handle portion causes the jaw members of the clamp portion to draw together;

a disk-like engaging member appended to the distal end of each of the jaw members; and a guide means for ensuring that the disk-like engaging members open and close with a linear vertical motion in a coaxial plane, the guide means being disposed on and connecting the first and second jaw members at a position intermediate of the pivot point and the distal end of the clamp portion of the jaw members wherein the guide means comprises:

a linear bearing member rigidly affixed at one end to one of the first or second jaw members, the linear bearing member including an elongate member having at least one elongate, vertically oriented slot therein for receiving and permitting vertical travel of the other of the first or second jaw members; and a means for biasing the clamp portion and the handle portion of the first and second jaw members apart from each other wherein the jaw member disposed within the elongate member of the linear bearing member, and adapted for vertical movement therein, forms a joint that is disposed within the slot to enable articulation of two segments of the jaw member that is disposed within the slot.

15. The device of claim 14 wherein low friction bearing elements are joined to at least one of the segments of the jaw member disposed within the slot.

16. The device of claim 14 wherein the means for biasing is disposed within the linear bearing member.

17. The device of claim 14 wherein the elongate member is a cylindrical member.

18. A patella clamp device, comprising first and second opposed jaw members joined to each other at a pivot point in a scissors-like orientation, the jaw members having a clamping portion at a distal end thereof and a handle portion at a proximal end thereof;

a vertically extending linear bearing member rigidly secured to the second jaw member intermediate of the pivot point and the distal end of clamping portion, the linear bearing member including a vertically oriented slot formed therein within which the first jaw member is disposed and adapted for vertical movement therein;

a joint formed in the clamp portion of the first jaw member separating the clamp portion into two segments, the joint being housed within the linear bearing member;

means for biasing the clamp portion and the handle portion of the jaw members apart from one another, the means for biasing being disposed within the linear bearing member;

a plurality of inclined teeth disposed on a surface of one of the first or second jaw members in proximity to the pivot point;

a pawl member mounted on the other of the first or second jaw members, the pawl being selectively engageable with the inclined teeth such that the pawl, when in the engaged position, permits closure of the jaw members but prevents opening of the jaw members; and means for selectively engaging the pawl member.

19. The device of claim 18 wherein the joint is formed by the engagement of a male member of one segment of the first jaw member within a vertically oriented female slot of the other segment of the first jaw member.

20. The device of claim 18 further comprising a low friction bearing element mounted on top and bottom portions of the female slot.

21. The device of claim 20 wherein the means for biasing is a spring element that is mounted within the linear bearing member between a bottom portion of the female slot and a bottom portion of the linear bearing member.

22. A patella clamp device, comprising first and second opposed jaw members joined to each other at a pivot point, each jaw member having a clamping portion distal to the pivot point and a handle portion proximal to the pivot point, the pivotal joinder of the first and second jaw members being such that force exerted to overcome a biasing force on the jaw members to draw together the jaw members of the handle portion causes the jaw members of the clamp portion to draw together;

a means for biasing the clamp portion and the handle portion of the first and second jaw members apart from each other;

a plurality of inclined teeth disposed on a surface of an intermediate portion of one of the first or second jaw members;

a pawl member mounted on an intermediate portion of the other of the first or second jaw members, the pawl member being selectively engageable with the inclined teeth such that the pawl, in the engaged position, permits closing of the jaw members but prevents opening of the jaw members; and means for selectively engaging the pawl member.

* * * * *